US010105526B2

(12) United States Patent
Scherr et al.

(10) Patent No.: US 10,105,526 B2
(45) Date of Patent: Oct. 23, 2018

(54) MICRONEEDLE SYSTEM AND METHOD FOR THE PRODUCTION THEREOF

(71) Applicant: LTS LOHMANN THERAPIE-SYSTEME AG, Andernach (DE)

(72) Inventors: Sebastian Scherr, Neuhaeusel (DE); Karsten Heuser, Bad Breisig (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 64 days.

(21) Appl. No.: 15/231,097

(22) Filed: Aug. 8, 2016

(65) Prior Publication Data

US 2016/0339223 A1    Nov. 24, 2016

Related U.S. Application Data

(63) Continuation-in-part of application No. PCT/EP2015/052150, filed on Feb. 3, 2015.

(30) Foreign Application Priority Data

Feb. 10, 2014  (EP) .................................... 14154481

(51) Int. Cl.
*A61M 37/00* (2006.01)
*A61B 5/15* (2006.01)
*A61B 17/20* (2006.01)

(52) U.S. Cl.
CPC ... *A61M 37/0015* (2013.01); *A61B 5/150022* (2013.01); *A61B 5/150282* (2013.01);
(Continued)

(58) Field of Classification Search
CPC ...... A61M 2037/0053; A61M 37/0015; A61M 2037/0023; A61M 2037/0046;
(Continued)

(56) References Cited

U.S. PATENT DOCUMENTS 6,230,051 B1 *  5/2001  Cormier ............ A61M 37/0015
                                                      600/573
6,537,264 B1    3/2003  Cormier et al.
                        (Continued)

FOREIGN PATENT DOCUMENTS

DE       697 30 971 T2     11/2005

OTHER PUBLICATIONS

US 2013/0331792 A1; Published Date: Dec. 12, 2013; Inventors: Jeffrey M. Karp, et al.
(Continued)

*Primary Examiner* — Lauren P Farrar
(74) *Attorney, Agent, or Firm* — R. S. Lombard

(57) ABSTRACT

A microneedle system and method for production thereof. From a board a web grating is produced which has a plurality of grating nodes each defined by three apertures and which has web grating wedges. The microneedle system comprising a board and a plurality of openings delimited circumferentially by a web grating, having at each opening at least one web grating wedge having a needle-shaped tip which projects from the board and which is oriented at least approximately normal to the board. Web grating wedges having needle-shaped tips protrude into each aperture from at least three different directions. In order to produce openings, at least all the web grating wedges which protrude into an aperture are bent by a punch and the needle-shaped tips thereof are oriented normal to the plane of the web grating. At least two web grating wedges are arranged at each opening.

7 Claims, 6 Drawing Sheets

(52) U.S. Cl.
CPC ...... *A61B 5/150984* (2013.01); *A61B 17/205* (2013.01); *A61M 2037/0023* (2013.01); *A61M 2037/0046* (2013.01); *A61M 2037/0053* (2013.01)

(58) Field of Classification Search
CPC ........ A61B 5/150022; A61B 5/150282; A61B 5/150984; A61B 17/205
See application file for complete search history.

(56) References Cited

U.S. PATENT DOCUMENTS

| | | |
|---|---|---|
| 2003/0198810 A1 | 10/2003 | Trautman et al. |
| 2003/0199810 A1* | 10/2003 | Trautman .......... A61M 37/0015 604/46 |
| 2005/0031676 A1 | 2/2005 | Wong et al. |
| 2005/0049549 A1 | 3/2005 | Wong et al. |
| 2008/0125743 A1 | 5/2008 | Yuzhakov |
| 2010/0305473 A1 | 12/2010 | Yuzhakov |
| 2013/0158482 A1 | 6/2013 | Davis et al. |

OTHER PUBLICATIONS

US 2007/0161964 A1 Published Date: Jul. 12, 2007; Inventor; Vadim V. Yushakov.

English translation of the International Search Report for the corresponding international application dated Apr. 16, 2015 (4 pages).

English translation of the Written Opinion of the International Searching Authority for the corresponding international application (13 pages), dated: Aug. 16, 2016.

English Translation of the International Search Report for the corresponding application dated Apr. 16, 2015 (4 pages).

* cited by examiner

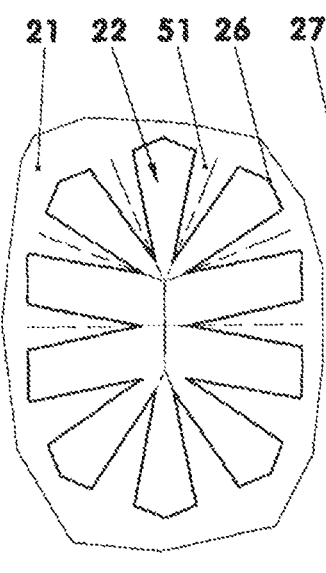
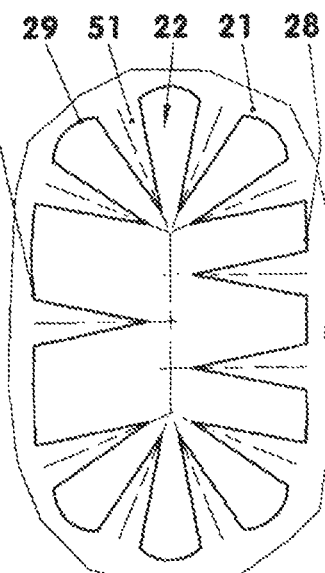
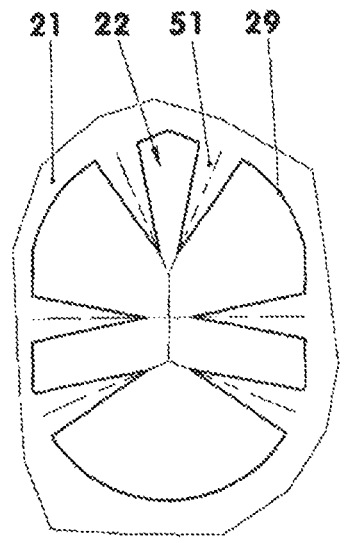
Fig. 7   Fig. 8   Fig. 9
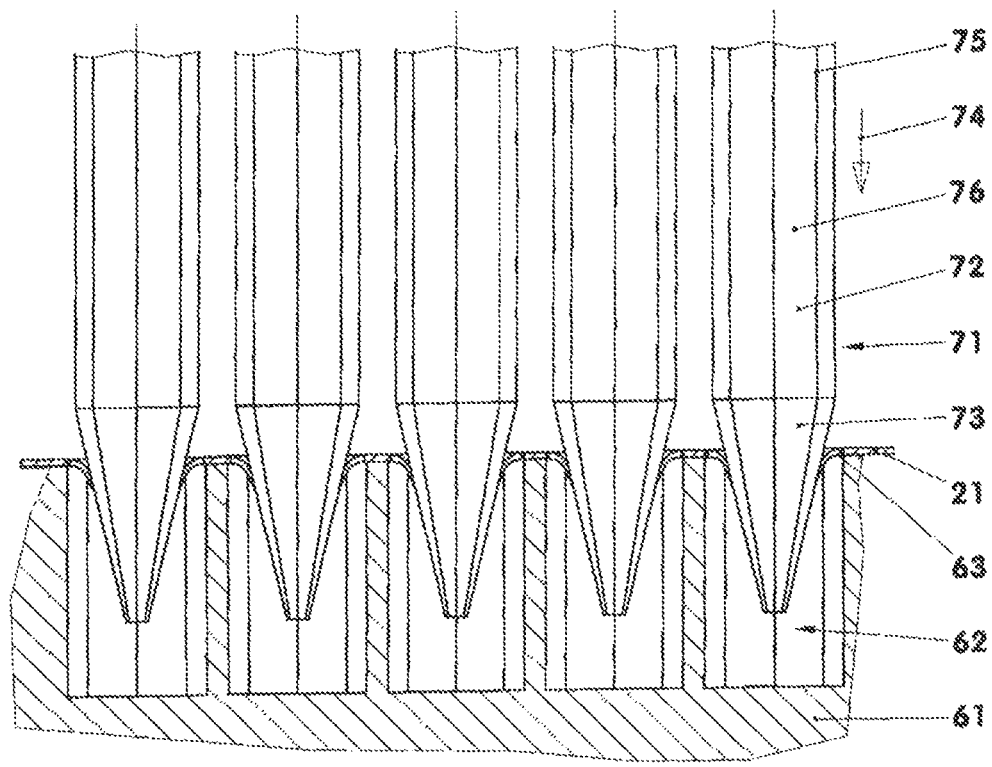
Fig. 10

MICRONEEDLE SYSTEM AND METHOD FOR THE PRODUCTION THEREOF

CROSS-REFERENCE TO RELATED APPLICATIONS

This is a continuation-in-part application of pending international application PCT/EP2015/052150 filed Feb. 3, 2015, and claiming the priority of European application No. 14154481.7 filed Feb. 10, 2014. The said International application PCT/EP2015/052150 and European application No. 14154481.7 are both incorporated herein by reference in their entireties as though fully set forth.

BACKGROUND OF THE INVENTION

The invention relates to a method for producing such a microneedle system, a web grid with a multiplicity of grid nodes which are defined by way of in each case three apertures and with web grid wedges being produced from a board, and to a microneedle system having a board and having a multiplicity of openings which are delimited peripherally by way of a web grid, at least one web grid wedge with a needle-shaped point which projects from the board and is oriented at least approximately perpendicularly with respect to the board being arranged at each opening, each web grid wedge comprising a bending zone with a bending line which is oriented parallel to the plane of the web grid, and the number of needle-shaped points corresponding at least to three times the number of openings.

According to US 2003/0199810 A1, an elastomeric material which is loaded by a large ram is used in the production of a microneedle system, which elastomeric material bends the in each case one point per aperture. Before processing, all the points point in the same direction. If a transverse load occurs during the application, the needles can buckle. The microneedle system becomes unusable.

According to DE 697 30 971 T2, needles which are offset with respect to one another can be arranged on opposite sides of an aperture. A transverse load can also lead to failure of the microneedle system in this embodiment.

The present invention is based on the problem of increasing the operational reliability of a microneedle system.

SUMMARY OF THE INVENTION

This problem is solved by way of the features of the independent claims. To this end, web grid wedges with needle-shaped points protrude into every aperture from at least three different directions during production. At least all the web grid wedges which protrude into an aperture are bent by means of a ram in order to produce openings, and their needle-shaped points are oriented perpendicularly with respect to the plane of the web grid.

The microneedle system which is produced in this way is constructed in such a way that at least two web grid wedges are arranged at each opening, the bending lines of which web grid wedges are not oriented parallel to one another. Moreover, in each case three openings define a grid node in the web grid.

BRIEF DESCRIPTION OF THE DRAWINGS

Further details of the invention arise from the claims and the following descriptions of diagrammatically shown exemplary embodiments:

FIG. 7 shows a variant of FIG. 6;
FIG. 8 shows a second variant of FIG. 6;
FIG. 9 shows a third variant of FIG. 6;
FIG. 10 shows the production of the openings.

DETAILED DESCRIPTION OF THE INVENTION

Figure 1:
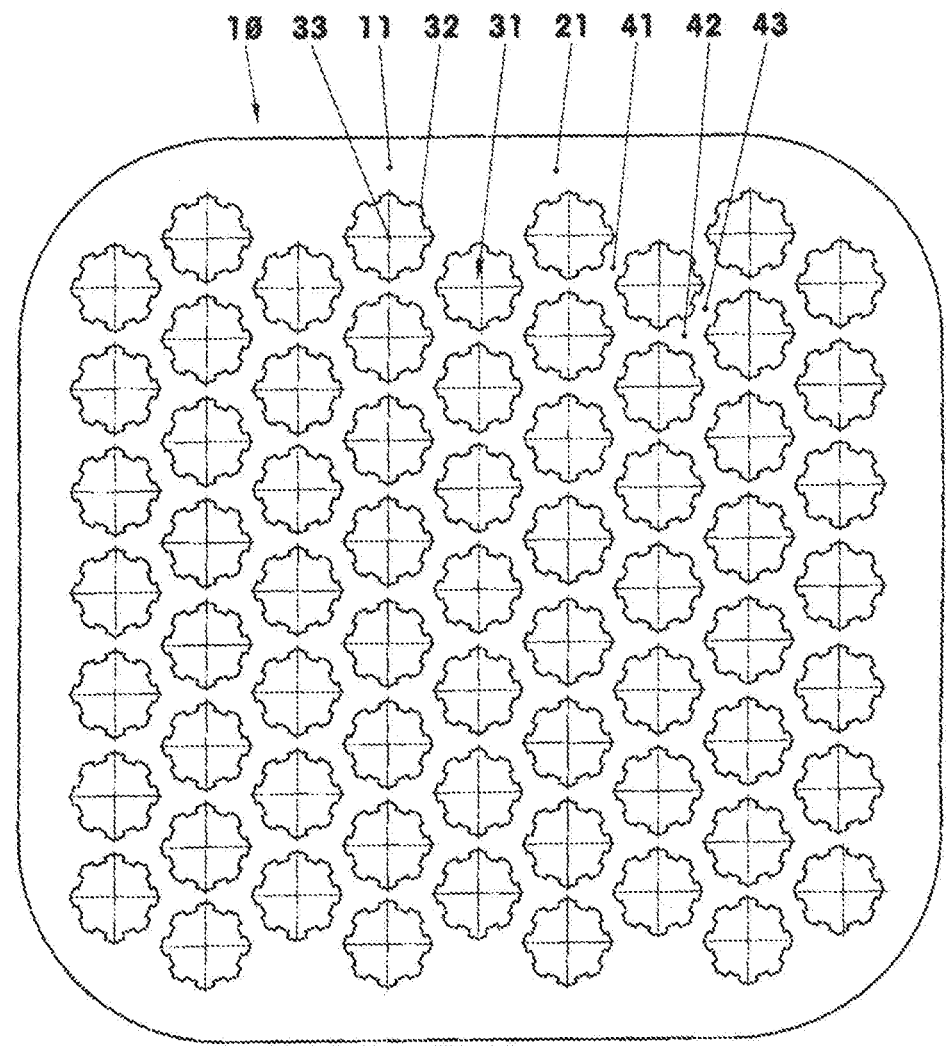
FIG. 1 shows a plan view of a board.
Figure 2:
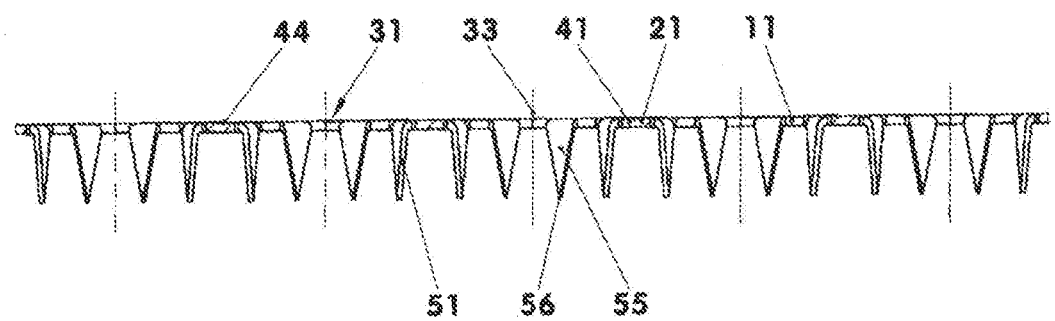
FIG. 2 shows a partial longitudinal section from FIG. 1.

FIG. 1 shows a plan view and FIG. 2 shows a longitudinal section of a microneedle system (10) from FIG. 1. Microneedle systems (10) of this type are used to introduce an active substance from an active substance reservoir (not shown here) through the skin into the body of a patient.

The active substance reservoir is arranged on an active substance carrier (11). Said active substance carrier (11) comprises a board (21) which comprises a web grid (41), a multiplicity of openings (31) and a multiplicity of needles (55). More than 30 openings (31) are arranged in the board (21) in the exemplary embodiment. Each opening (31) is delimited by eight needles (55). Each needle (55) has a point (56). The openings (31) have a closed contour in the exemplary embodiment which is shown. For example, they have the design of an octagon in basic shape, the corners (32) of which are arranged between the individual needles (55). The basic shape can also be a regular or irregular triangle, quadrangle, hexagon, etc. An embodiment of the basic shape as a circle, ellipse, oval, etc. is also conceivable.

In the exemplary embodiment which is shown, the board (21) has a length of 20 mm and a width of 20 mm. The corners are rounded with a corner radius of 5 mm. The thickness of the board (21) is 0.1 mm. In this exemplary embodiment, the board is produced from an austenitic, corrosion-resistant and acid-resistant material. This is, for example, X5CrNi18-10 with the material number 1.4301.

67 openings (31) are arranged in the board (21) which is shown in FIG. 1. The sum of the cross-sectional areas of all openings (31) is 40% of the basic area of the board (21) in this exemplary embodiment. The sum of the cross-sectional areas of all openings (31) is therefore greater than 30% of the basic area of the board (21).

The openings (31) are surrounded by the web grid (41). In each case three openings (31) define a grid node (42). Three webs (43) are connected to one another in a T-shaped manner at each grid node (42).

Figure 3:
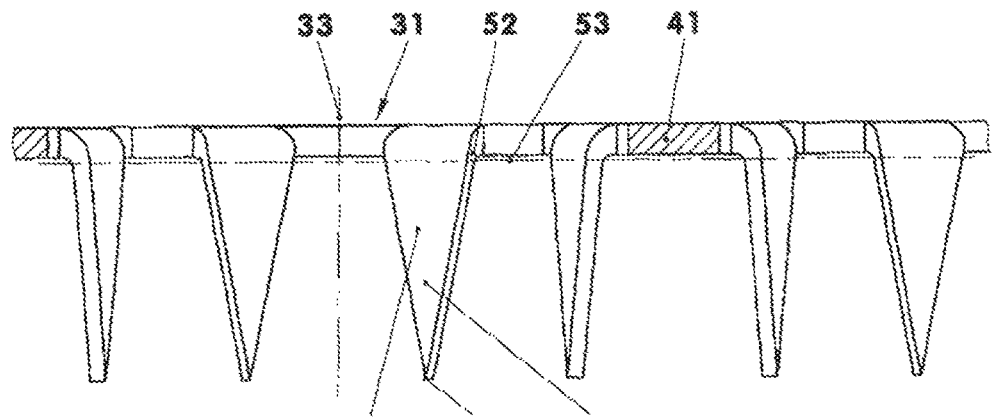
FIG. 3 shows a detail from FIG. 2.

The web grid (41) lies in a plane, out of which web grid wedges (51) protrude perpendicularly with respect to said plane. In the illustration of FIG. 2, they protrude downward. Each web grid wedge (51) comprises a bending zone (52) which is connected to the web grid (41), and a needle (55) (cf. FIG. 3). The points (56) of the individual needles (55) are configured by the center axis (33) of the opening (31) symmetrically with respect to the center longitudinal plane of the web grid wedges (51) which is oriented in the thickness direction of the board. The thickness of the individual web grid wedge (51) corresponds to the thickness of the board (21). The bending zone (52) has a constant bending radius which corresponds, for example, to the thickness of the web grid wedge (51). The web grid wedges (51) therefore protrude out of the web grid (41) at least by 80% of their length. In the exemplary embodiment, the needles (55) project out of the web grid (41) at least by 0.6 mm.

At least three web grid wedges (51) are arranged at an opening (31). In the present exemplary embodiment, each of the openings (31) is delimited by the same number of web grid wedges (51). The bending lines (53) of at least two web grid wedges (51) point in different directions. Said two bending lines have a point of intersection. In the exemplary embodiment, the straight bending lines of in each case two bending zones (52) have the same direction.

Figure 4:
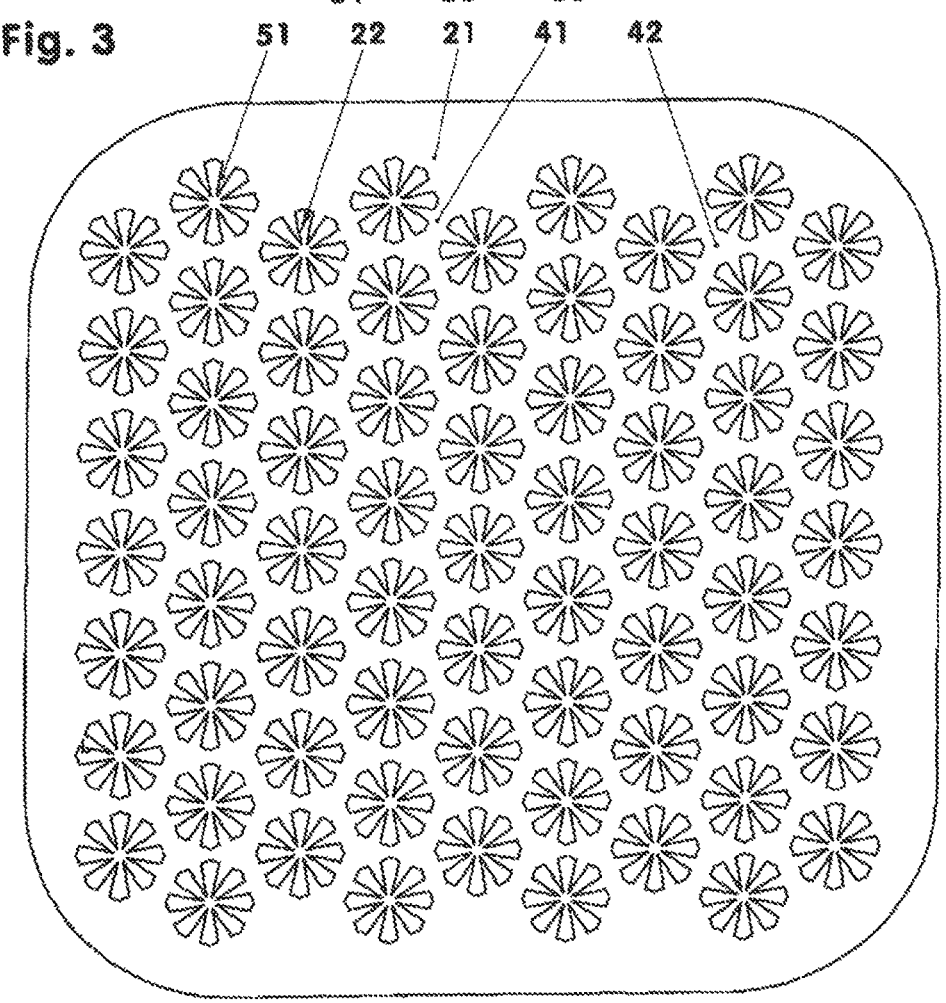
FIG. 4 shows a board with apertures.
Figure 5:
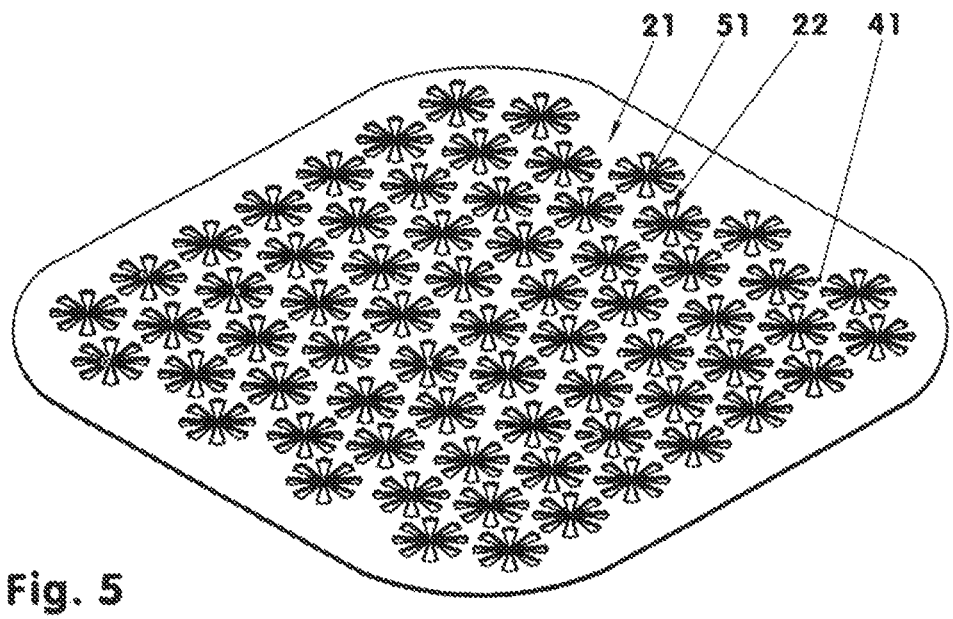
FIG. 5 shows a diametric view of FIG. 4.
Figure 6:
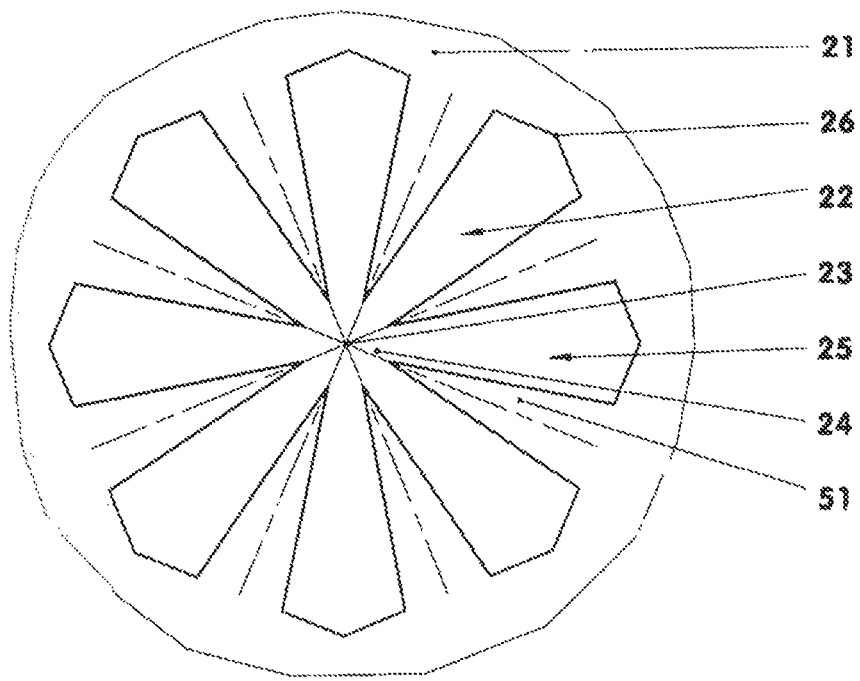
FIG. 6 shows a detail from FIG. 4.
Figure 11:
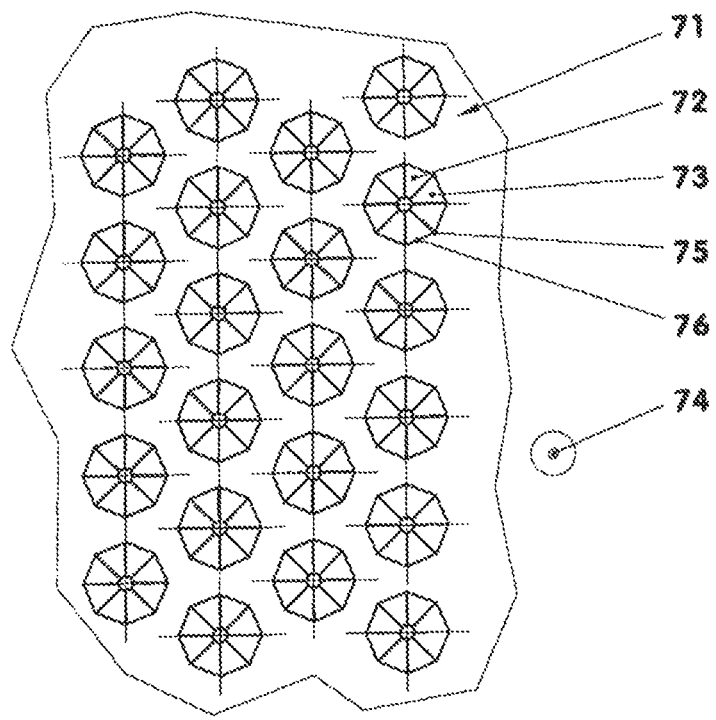
FIG. 11 shows a plan view of a ram system.
Figure 12:
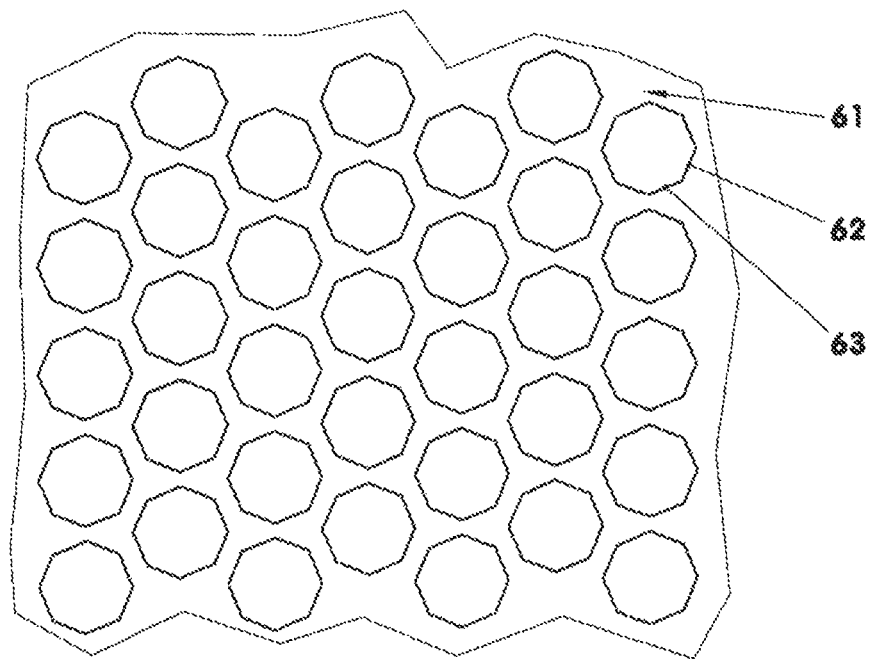
FIG. 12 shows a plan view of a matrix system.

The production of the microneedle system (10) is shown in FIGS. 4-6 and in FIGS. 10-14. The starting material is, for example, a flat board (21) of constant thickness made from the abovementioned material. In the exemplary embodiment, it has a square base area with rounded corners. The board (21) can also be of round, angular, elliptical, etc. configuration.

First of all, apertures (22) are made in said metal sheet. This takes place by way of punching, laser cutting, etching, etc. As shown in FIGS. 4 and 5, the individual apertures (22) are arranged, for example, in rows which lie next to one another. The individual rows are offset with respect to one another by half a pitch. The center lines (23) of in each case three apertures (22) which are adjacent with respect to one another form a wedge with an equilateral triangle as base area. Here, the center point spacing of two adjacent apertures (22) from one another is greater by 15% than the diameter of the circumcircle of a single aperture (22).

FIG. 6 shows the detail of an aperture (22). It comprises a central region (24) and, for example, eight outwardly widening aperture sections (25) which are arranged radially with respect to the center line. Each of said aperture sections (25) is symmetrical with respect to a radial line of the aperture (22), each of said radial lines intersecting an outer corner (26) of the aperture (22).

After the punching-out operation, for example, the web grid (41) and the web grid wedges (51) between the aperture sections (25) remain of the original board (21). The web grid wedges (51) which are, for example, triangular in the plan view of FIG. 6 are arranged between the corners (26) of the aperture (22) and protrude with a length of, for example, 0.75 mm out of the web grid (41). In said plan view, the width of the individual web grid wedge (51) is 0.3 mm. In said exemplary embodiment, the area of all web grid wedges (51) in the plan view is 34% of the area of the basic shape of the aperture (22), which basic shape is defined by way of the corners (26). The area of all web grid wedges (51) is between 25% and 50% of the basic shape of the aperture (22), which basic shape is, for example, octagonal here. On account of these proportions, there is no risk of damaging the web grid wedges (51) during the production of the apertures (22).

The individual apertures (22) are arranged with respect to one another in such a way that the web grid wedges (51) are not aligned with one another. In the plan view of FIG. 4, the aperture sections are aligned with one another in the individual gaps. In adjacent gaps, a web grid wedge (51) is arranged adjacently with respect to an aperture section (25).

FIGS. 7-9 show variants of the design of apertures (22). In FIG. 7, the basic shape of the aperture (22) has 10 corners (26). Said basic shape including the web grid wedges (51) is symmetrical with respect to a center longitudinal plane of the aperture (22). The individual web grid wedge (51) is also arranged between two corners (26) of the aperture (22) in said exemplary embodiment. Instead of the corners (26), arcs can also be arranged between the web grid wedges (51).

The aperture (22) which is shown in FIG. 8 has two longitudinal sides (27, 28) which lie opposite one another. A single web grid wedge (51) is arranged on the one longitudinal side (27). Offset with respect thereto, two web grid wedges (51) are seated on the other longitudinal side (28).

FIG. 9 shows an aperture with six web grid wedges (51). In said plan view, in each case two web grid wedges (51) point toward a common point of the vertical center longitudinal plane. Instead of the corners (26), arcuate elements (29) are arranged between the individual web grid wedges (51).

The board (21) with the apertures (22) is inserted, for example, into a bending press (cf. FIG. 10). The bending press comprises a matrix system (61) and a ram system (71). The matrix system (61) (cf. FIG. 12) comprises a multiplicity of recesses (62) in the exemplary embodiment. The number of recesses (62) corresponds to the number of apertures (22) of the board (21). The cross-sectional area of the individual recess (62) is octagonal. The recess (62) has a rounded portion (63) at its upper edges (cf. also FIG. 10). Said rounded portion (63) has, for example, a radius of 0.2 mm. The inner cross section of the recess (62) is smaller by the rounded portions (63) than the cross section of the basic shape of the aperture (22).

The ram system (71) (cf. FIG. 11) comprises a multiplicity of rams (72). Said rams (72) which are identical in the exemplary embodiment have an octagonal cross-sectional area in the exemplary embodiment. The flats width is narrower, for example, by twice the thickness of the board (21) than the corresponding dimension of the recess (62) of the matrix system (61). The tip (73) of the individual ram (72) is configured in the shape of a truncated pyramid. The tip angle is, for example, 30°.

In the bending press, the ram system (71) is moved toward the matrix system (61). The board (21) is held in its position, for example by means of hold-downs. The rams (72) make contact with the web grid wedges (51) and dip into the matrixes (62). Here, the web grid wedges (51) are bent along the rounded portions (63) of the respective matrix (62). The forming can take place in a cold or warm manner. The respective bending zone (52) has a straight bending line (53). All bending lines (53) lie in a common plane which is parallel to the plane of the upper side (44) of the web grid (41). The bending lines (53) of the web grid wedges (51) thus have four different directions. Since no regions which are adjacent with respect to one another are deformed on account of the arrangement and the orientation of the apertures (22), the web grid (41) retains its static strength. There is no risk of buckling of the web grid wedges (51). Geometrically simple tools can be used both for producing the apertures (22) and for forming. For example, only a single ram (72) is used for each aperture (22). By means of said ram (72), all (for example, eight) needles (55) are produced from the web grid wedges (51) in a single ram stroke.

Figure 13:
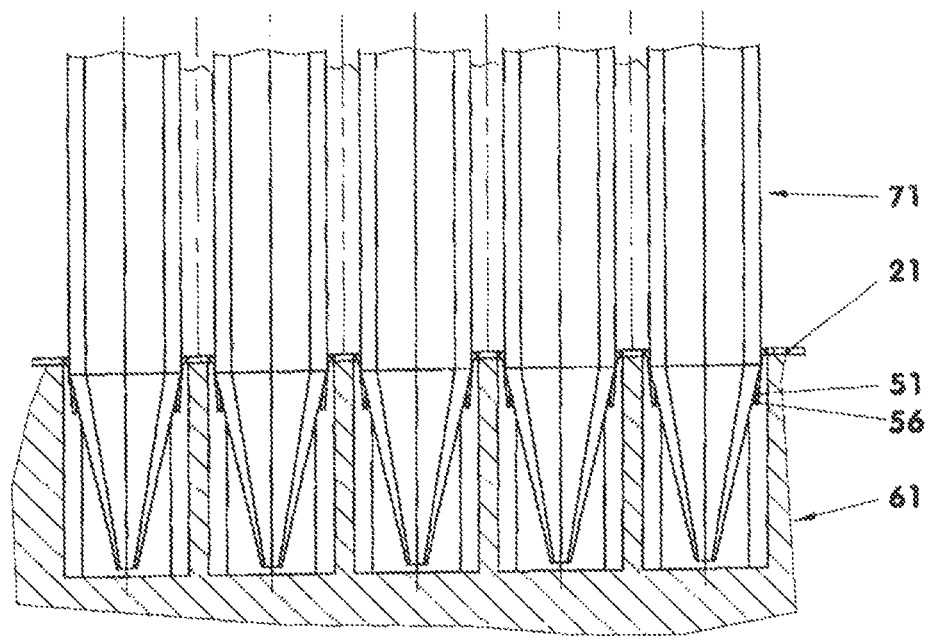
FIG. 13 shows a ram with a reshaped board; and,
FIG. 14 shows a diametric view of a board after reshaping.

During further dipping of the rams (72) into the matrixes (62), the web grid wedges (51) are deformed further until they project perpendicularly with respect to the plane of the web grid (41). The points (56) of the web grid wedges (51) now point in the direction which faces away from the plane of the web grid (41). This is shown in FIG. 13. Depending on the forming process, the ram (72) can be kept in said position during a predefined time interval or can slightly overstretch the web grid wedges (51).

Figure 14:
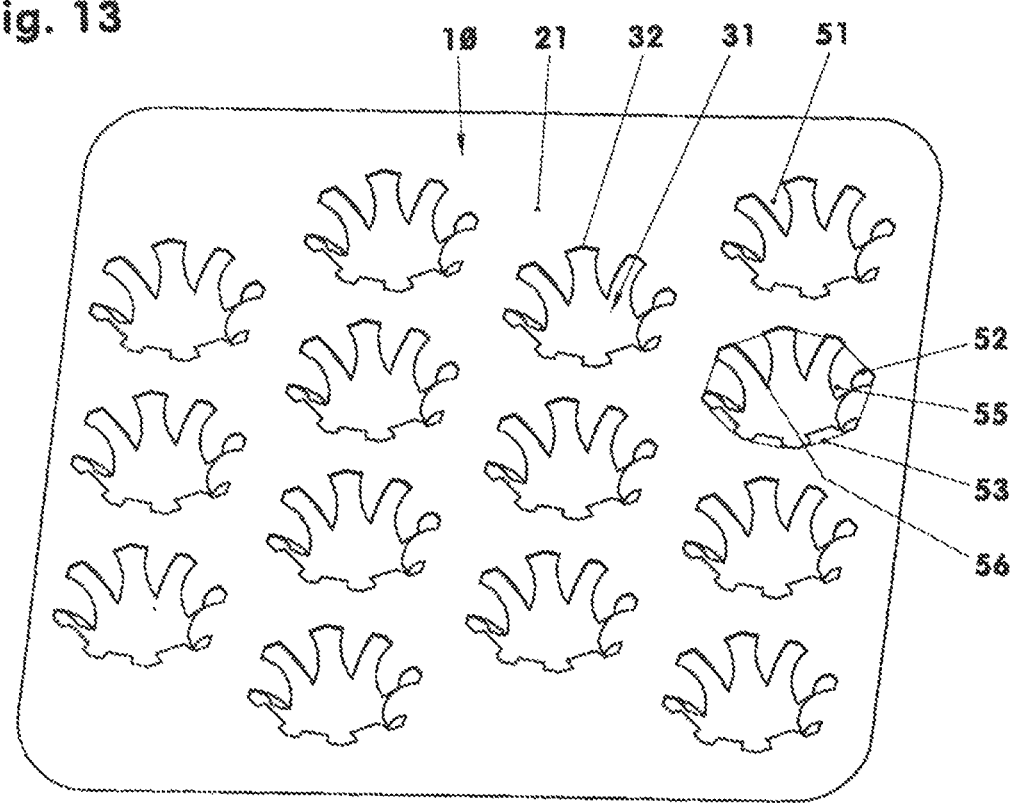

The web grid wedges (51) now form the needles (55) which, in the illustration of FIG. 14, surround the openings (31) and project downward. For example, the needles (55) project with a length of 0.6 mm out of the web grid (41). In the exemplary embodiment of FIG. 14, 1.2 needles are arranged per square millimeter of board area, on the basis of the abovementioned dimensions. In the case of a microneedle system (10) which is produced from the board (21) according to FIGS. 4 and 5, 1.4 needles (55) are arranged per square millimeter of the board area. In relation to the area of the openings (31), the exemplary embodiments have at least three needles (55) and points (56) per square millimeter of the opening cross section. The overall area of the openings (31) is, for example, more than 30% of the base area of the board (21).

In order to use the microneedle system (10), it is placed with a mounted active substance reservoir onto the skin of the patient and is pressed into said skin. Here, the user introduces substantially a force which is oriented in the direction of the needles (55). The needles (55) overcome the resistance of the upper skin layers and penetrate into the skin. For example, resistances of the skin and/or an oblique application of force by the user can lead to shear forces on the needles (55). On account of the different directions of the bending lines (53) of the individual needles (55) there is no risk of buckling or bending of the needles (55) during the use of the described microneedle system (10). All the needles (55) therefore penetrate into the skin of the patient.

After the application of the microneedle system (10), the active substance penetrates through the openings (31) into the skin which is tensioned between the microneedles (55). Here, the volumetric flow of the active substance is greater, the greater the ratio is of the overall area of the openings (31) to the basic area of the board (21). For example, the volumetric flow rises proportionally with respect to a rising ratio. On account of the arrangement of the needles (55) along closed contours, the area of the web grid (41) can be can be selected to be small in comparison with the overall area of the openings (31), with an identical number of needles (55). The factor can be, for example, less than 2.5.

In order to produce the microneedle system (10), only two work operations are required. In both work operations, the tools in each case perform a single stroke movement. The microneedle system (10) can therefore be produced rapidly and without problems. It is therefore suitable for mass production.

It is also conceivable to combine the various stated embodiments with one another.

LIST OF REFERENCE SIGNS

10 Microneedle system
11 Active substance carrier
21 Board
22 Apertures
23 Center lines
24 Central region
25 Aperture sections
26 Corner
27 Longitudinal side
28 Longitudinal side
29 Arcuate elements
31 Openings
32 Corners
33 Center axis
41 Web grid
42 Grid node
43 Webs
44 Upper side
51 Web grid wedges
52 Bending zones
53 Bending lines
55 Needles, microneedles
56 Points, needle-shaped points
61 Matrix system
62 Recesses, matrixes
63 Rounded portion
71 Ram system
72 Ram
73 Ram tip
74 Stroke direction
75 Longitudinal edges
76 Ram face

What is claimed is:

1. A method for producing a microneedle system (10), said microneedle system (10) including,
    a web grid (41) with a multiplicity of grid nodes (42) which are defined by way of in each case three apertures (22) and each of the grid nodes (42) having three webs (43) connected to one another in a T-shaped arrangement and each of said apertures (22) arranged with respect to each other with web grid wedges (51) not aligned with one another being produced from a board (21),
    the web grid wedges (51) each with needles (55) having needle-shaped points (56) protruding into every aperture (22) from at least three different directions before bending of the web grid wedges (51) along a bending line (53), and said method including the following steps:
    at least all the web grid wedges (51) which protrude into an aperture (22) from at least three different directions prior to bending, being bent by a single rain (72) in a single rain stroke in order to produce the needles (55) having needle-shaped points (56) at openings (31), each of the web grid wedges (51) being bent along the bending line (53) in a common plane parallel to an upper side (44) of the web grid (41), at least two of the web grid wedges (51) which protrude into an aperture (22) having bending lines (53) pointing in different directions, and the needle-shaped points (56) of the needles (55) being oriented perpendicularly with respect to the plane of the web grid (41).

2. The method for producing a microneedle system (10) of claim 1, wherein the rain (72) has longitudinal edges (75) which are oriented in its stroke direction (74), in each case two longitudinal edges (75) delimiting a planar rain face (76).

3. The method for producing a microneedle system (10) of claim 1, wherein the board (21) which has the apertures (22) lies on a matrix system (61) with at least one recess (62) with a polygonal cross section.

4. A microneedle system (10) comprising:
    a board (21) and having a multiplicity of openings (31) which are delimited peripherally by way of a web grid (41), at least three web grid wedges (51) operatively arranged at each of the openings (31), each of the web grid wedges (51) with a needle (55) having a needle-shaped point (56) which projects from the web grid (41) and is oriented at least approximately perpendicularly with respect to the plane of the web grid (41), each web grid wedge (51) comprising a bending zone (52) with a bending line (53) which is oriented parallel to the plane of the web grid (41), and the number of needle-shaped points (56) corresponding at least to three times the number of openings (31),
wherein at least two of the at least three web grid wedges (51) are arranged at each opening (31); such that the bending lines (53) of the at least two of the at least three web grid wedges (51) arranged at each opening (31) are not oriented parallel to one another, and
wherein in each case three openings (31) of the board (21) define a grid node (42) in the web grid (41) having three webs (43) connected to one another in a T-shaped arrangement at each of said grid nodes.

5. The microneedle system (10) of claim 4, wherein the overall cross-sectional area of the openings (31) is at least 30% of the board base area.

6. The microneedle system (10) of claim 4, wherein the bending lines (53) of in each case two adjacent web grid wedges (51) intersect at precisely one point.

7. The microneedle system (10) of claim 4, wherein all of the needle-shaped points (56) are parts of needles (55) which have at least approximately the same length.

\* \* \* \* \*